(12) United States Patent
Rothblat et al.

(10) Patent No.: US 7,060,452 B2
(45) Date of Patent: Jun. 13, 2006

(54) ASSAY METHOD FOR MEASUREMENT OF NET CHOLESTEROL FLUX

(75) Inventors: George H. Rothblat, Philadelphia, PA (US); Ginny Kellner-Weibel, Harleysville, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 450 days.

(21) Appl. No.: 10/264,191

(22) Filed: Oct. 3, 2002

(65) Prior Publication Data

US 2003/0082617 A1 May 1, 2003

Related U.S. Application Data

(60) Provisional application No. 60/326,831, filed on Oct. 3, 2001.

(51) Int. Cl.
*C12Q 1/60* (2006.01)
(52) U.S. Cl. .................................................. 435/11
(58) Field of Classification Search .................. 435/11
See application file for complete search history.

(56) References Cited

OTHER PUBLICATIONS

Rothblat et al., "Cell cholesterol efflux: integration of old and new observations provides new insights", J. Lipid Research 40 : 781-796 (1999).*
Shio, H., et al., "Characterization of Lipid-Laden Aortic Cells from Cholesterol-Fed Rabbits"; Lab. Invest. 39: 390-397 (1978).
Small, D. M., "Progression and Regression of Atherosclerotic Lesions"; Arteriosclerosis, 8: 103-129 (1988).
Contreras, J. A., et. al., "Essential Differences in Cholesteryl Ester Metabolism Between Human Monocyte-Derived and J774 Macrophages"; Arterioscler. Thromb. 14: 443-452 (1994).
Hakamata, H. et. al., "Species Difference in Cholesteryl Ester Cycle and HDL-Induced Cholesterol Efflux From Macrophage Foam Cells"; Arterioscler. Thromb. 14: 1860-1865 (1994).
Johnson, W. J., et. al., "Cholesterol transport between cells and high-density lipoproteins"; Biochim. Biophys. Acta. 1085: 273-298 (1991).
Hakamata, H., et. al., "Differential effects of an acyl-coenzyme A:cholesterol acyltransferase inhibitor on HDL-induced cholesterol efflux from rat macrophage foam cells"; FEBS 363: 29-32 (1995).
Johnson, W. J., et. al., "The Bidirectional Flux of Cholesterol between Cells and Lipoproteins"; J. Biol. Chem. 261:5766-5776 (1986).
Bernard, D. W., et. al., "cAMP Stimulates Cholesteryl Ester Clearance to High Density Lipoproteins in J774 Macrophages"; J. Biol. Chem. 266: 710-716 (1991).
Miyazaki, A., et. al., "Acetylated Low Density Lipoprotein Reduces its Ligand Activity for the Scavenger Receptor after Interaction with Reconstituted High Density Lipoprotein"; J. Biol. Chem. 269: 5264-5269 (1994).
Fofana, M., et al., "Transfer of cholesterol between high density lipoproteins and cultured rat Sertoli cells", Biochem. Cell Biol., 74: 681-686 (1996).
Fournier, N., et al., "Fractional efflux and net change in cellular cholesterol content mediated by sera from mice expressing both human apolipoprotein Al and human lecithin: cholesterol acyltransferase genes", Atherosclerosis, 147: 227-235 (1999).
Atger, V.M., et al., "Cyclodextrins as Catalysts for the Removal of Cholesterol from Macrophage Foam Cells", J. Clin. Invest., vol. 99: 773-780, (1997).

* cited by examiner

*Primary Examiner*—Sandra E. Saucier
(74) *Attorney, Agent, or Firm*—Dann Dorfman Herrell and Skillman; Kathleen D. Rigaut

(57) ABSTRACT

The present invention relates to an assay for determining net cholesterol flux from lipid loaded cells in the presence of an acceptor (e.g., serum). The present invention also relates to a method for evaluating efficacy of a therapeutic agent for stimulating or inhibiting net cholesterol flux. Also provided by the present invention are kits that are used to carry out the aforementioned assays and methods.

3 Claims, 6 Drawing Sheets

US 7,060,452 B2

ASSAY METHOD FOR MEASUREMENT OF NET CHOLESTEROL FLUX

CONTINUING APPLICATION DATA

This application claims priority under 35 U.S.C. §119 (e) to U.S. Provisional Patent Application No. 60/326,831 filed on Oct. 3, 2001, the entire disclosure of which is incorporated by reference herein.

FIELD OF THE INVENTION

The present invention relates to the fields of diagnostic testing and cholesterol metabolism. More specifically, assays are provided for determining net cholesterol flux following exposure of lipid loaded cells to patient serum samples.

BACKGROUND OF THE INVENTION

Several publications and patent documents are referenced in this application in order to more fully describe the state of the art to which this invention pertains. Full citations for these references are found within and at the end of the specification. The disclosure of each of these publications is incorporated by reference herein.

Atherosclerosis is a leading cause of death in the United States and results from the formation of plaques in arterial walls that often occlude the vessel lumen and obstruct blood flow. Morbidity and mortality generally occur through end organ damage and organ dysfunction resulting from ischemia. The most common forms of ischemic end organ damage are myocardial infarction and cerebrovascular accidents. Disability or death often result from these vascular events. Atherosclerosis-related ischemia that does not permanently injure myocardium often causes anginapectoris and congestive heart failure. Additionally, atherosclerotic occlusions may damage other organs, such as the kidneys, the intestines, and the spinal cord. These occlusions consist of plaques that form by accumulation of cholesterol, cholesterol esters, and phospholipids and the proliferation of smooth muscle cells in the intima of major arteries. Lipid contributes a major portion of the plaque volume (generally 30–65% dry weight). In fact, the risk of developing arteriosclerosis is directly related to the concentration of certain forms of plasma cholesterol.

Delivery of cholesterol into cells occurs via the receptor-mediated LDL pathway and by passive exchange of sterol between plasma membranes and lipoproteins. Only tissues that produce steroid hormones and bile acids can metabolize cholesterol. In order to prevent accumulation of excess free sterol in remaining peripheral tissues there is a reverse transport of cholesterol from plasma membranes into HDL and lipoprotein-like particles. HDL transports excess cholesterol to the liver where it can either be processed into bile salts for excretion or incorporated into very low density lipoproteins (VLDL) to re-enter the lipoprotein pool.

Assays that are currently available to measure cholesterol movement often employ isotopically labeled cholesterol to measure the movement of unesterified cholesterol (free cholesterol, FC) into (influx) or out of (efflux) cells. However, these assays have several disadvantages. First, the movement of cholesterol between cells and serum is bidirectional, thus net cholesterol flux is determined by the relative contribution of cholesterol influx and cholesterol efflux. Currently available assays measure cholesterol efflux only, and therefore fail to account for cholesterol influx. Measurements obtained from these assays could be inaccurate and misleading. Second, because these currently available assays measure the efflux of unesterified cholesterol, they cannot account for the pool of EC in atherogenic cells which is the major form of cholesterol present in foam cells both in vitro and in vivo (3, 4). Finally, inasmuch as non-human macrophage cells are used in such assays, they are not ideally suited for testing therapeutic agents for the treatment of human subjects.

SUMMARY OF THE INVENTION

It is an object of the present invention to provide a standard assay for determining net cholesterol flux from lipid loaded cells following exposure to a serum sample. The present invention also provides a method for evaluating efficacy of therapeutic agents in stimulating or inhibiting net cholesterol flux in a subject. It is still another object of the present invention to provide a kit useful for performing assays disclosed herein.

DETAILED DESCRIPTION OF THE INVENTION

Figure 1:
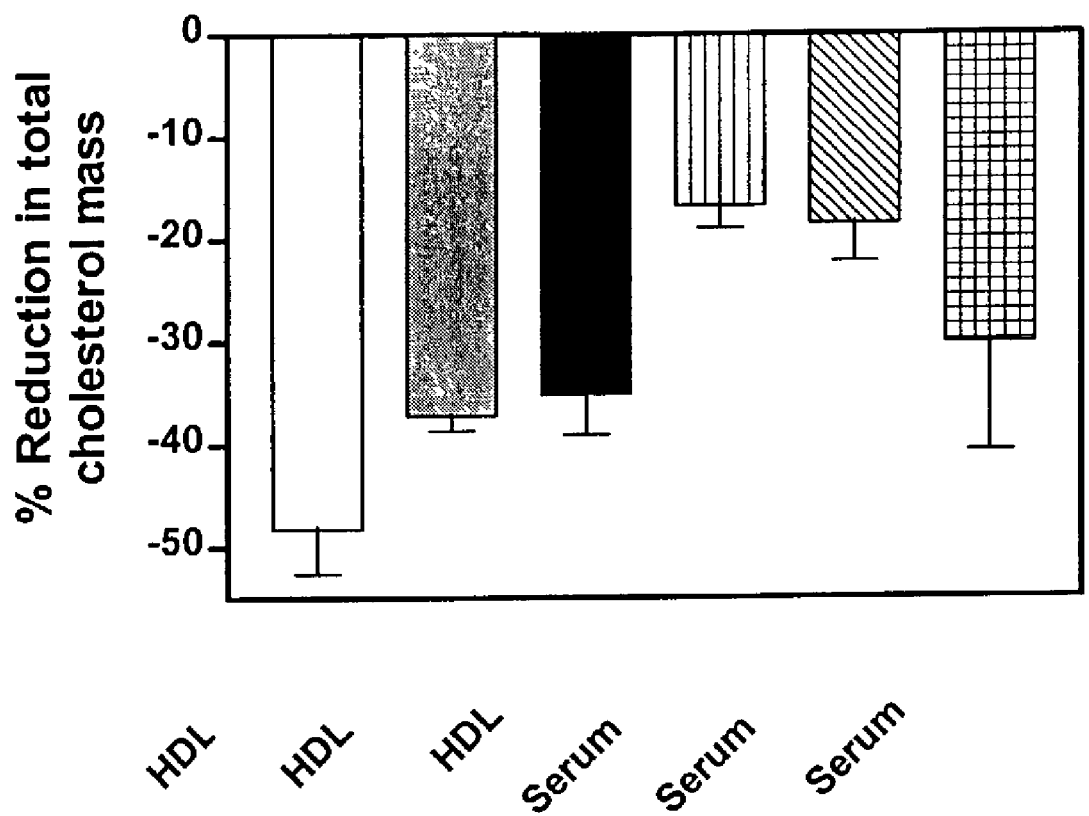
FIG. 1 is a graph showing the results obtained following incubation of THP-2 macrophage foam cells with various acceptors (e.g., HDL and serum). THP-1 macrophage were cholesterol enriched by growth in 100 μg/ml acLDL for 48 hours. The cells were then incubated with 10% human serum or 50 μg/ml HDL for 48 hours. Cholesterol mass was measured by GLC and values were normalized to total cell protein levels. Values are expressed percent change (decrease) relative to acLDL alone (no acceptor) which was set at zero.

Heart disease remains the leading killer in the United States despite healthier lifestyles and pharmaceutical intervention. The reduction of the initiation and progression of atherosclerosis by eliminating accumulation of lipid within vessel walls provides a therapeutically valuable approach for the prevention of cardiovascular disease.

The majority of lipid present in early atherosclerotic plaques is in the form of esterified cholesterol (EC) contained within macrophage-derived foam cells. A sensitive net cholesterol mass flux assay has been developed in accordance with the present invention. In one embodiment, a macrophage foam cell model is utilized to measure changes in total cholesterol (both EC and FC) mass when exposed to extracellular cholesterol acceptors (serum). In an alternative embodiment, macrophage cells containing basal levels of cholesterol are utilized in the assay. By incubating these cholesterol "normal" cells with a donor (acLDL) and an acceptor (e.g., serum or isolated lipoprotein) simultaneously, the acceptor's ability to promote or prevent the deposition of donor-derived cellular cholesterol can be evaluated. A standardized assay according to the invention can be used to screen whole sera, isolated lipoproteins, or other sera components from subjects on lipoprotein modifying therapies for the potential to move a measurable amount of cholesterol mass as opposed to the isotopic trace levels measured by traditional flux studies. In a further aspect, data obtained using this assay can be used to advantage in evaluating the effectiveness of lipoprotein modifying pharmaceuticals.

In an exemplary assay, net cholesterol flux is assessed by 1) contacting cholesterol enriched cells with a serum sample (an acceptor) and 2) quantifying the cellular cholesterol mass from the cholesterol enriched cells after exposure to the serum sample, wherein a reduction of the cellular cholesterol mass compared to that determined prior to the exposure to said serum sample correlates with the cholesterol clearance potential of the serum sample. In a specific embodiment of the present invention, the cholesterol enriched cells are foam cells.

Alternatively, the cholesterol enriched cells are obtained by incubating normal or recombinant cells that express one or more LDL-receptors or scavenger receptor with a cholesterol donor, such as native LDL, acetylated LDL (acLDL), oxidized LDL (oxLDL), aggregated LDL, or derivatives thereof. The cholesterol enriched cells may also be enriched with free cholesterol (unesterified) by culturing with a cholesterol donor in the presence of a ACAT inhibitor, including without limitation, CP-113,818 (Pfizer Pharmaceuticals) and 58-035 (Sandoz Pharmaceuticals). In a further embodiment of the present invention, the serum obtained from the subject is the HDL-containing fraction of the serum wherein apoB containing lipoproteins are removed.

Exemplary methods for evaluating efficacy of a therapeutic agent in stimulating or inhibiting net cholesterol mass flux in a subject comprise the steps of: 1) administering the therapeutic agent to the subject; 2) obtaining a serum sample from the subject after suitable time period; and 3) determining the the effect of the serum sample (acceptor) on net cholesterol mass flux by the assay disclosed above, wherein an increase or reduction of net cholesterol flux compared to that determined prior to the administration of therapeutic agent indicates the capacity of that agent to influence cholesterol flux. Also provided by the present invention are kits that are used to carry out the assays disclosed herein. Such kits may contain cholesterol enriched cells, culture medium, culture tubes or multi-well plates, and reagents to perform accurate measurement of cellular cholesterol mass.

Suitable therapeutic agents include drugs, prodrugs, nutraceuticals, and ligands that may modulate net cholesterol flux. The therapeutic agent is administered or dosed in accordance with good medicine practice, taking into account the clinical condition of the individual subject and other factors known to medical practitioners. The "effective amount" for purposes herein is refers to that amount of the therapeutic agent which results in a beneficial therapeutic effect (e.g. serum cholesterol reduction).

Cellular cholesterol mass is the level of total cholesterol (FC and EC) in the cells. It may be measured by any suitable assay, including, but are not limited to, enzymatic or chemical based assays. Such assays include Wako enzymatic assay kits for free and total cholesterol (Biochemical Diagnostics, Edgewood, N.J.), and the assay described by Rudel and Morris in Rudel, L. L., and Morris, M. D. (1973) Determination of Cholesterol using o-phthaldehyde, J. Lipid Res., 14:364–366. In one particular embodiment of the present invention, gas-liquid chromatography (GLC) was utilized in measuring the total cholesterol mass.

The following definitions are provided to facilitate an understanding of the present invention.

The phrase "net cholesterol flux" refers to the net movement of cholesterol mass determined by the changes of cellular cholesterol mass. It is the net result of the relative contribution of both cholesterol influx (in to the cell) and cholesterol efflux (out of the cell).

"Cholesterol influx" refers to the delivery of cholesterol into cells via the LDL-receptor-mediated LDL pathway and by passive exchange of sterol between plasma membranes and lipoprotein.

"Cholesterol efflux" refers to the reverse transport of cholesterol from plasma membranes into HDL and lipoprotein-like particles.

"Cellular cholesterol mass" is the total cellular cholesterol level and includes both esterified (EC) and unesterified cholesterol (FC).

The term "a subject" as used herein refers to both humans and other mammals. The term includes but is not limited to, mammalian, bovine, ovine, porcine, equine, rodent and human subjects.

"Cholesterol enriched cells" are cells that retain a cellular cholesterol level of about 80–100 µg/mg cell protein. Preferred cell types are macrophage cells, including both primary and transformed macrophage cells. The cells may be of human or non-human origin. Examples of non-human macrophage cells include, but are not limited to, JC774 mouse macrophage cells (ATCC# HB-197), RAW 264.7, primary mouse macrophages from wild type and transgenic mice. Examples of human macrophage cells include, but are not limited to, primary macrophage cells, THP-1 or THP-2 cells (ATCC# TIB-202), U937 (ATCC# CRL-1593.2), and primary human macrophages. Alternatively, cells that are transfected with one or more LDL-receptor genes may be used in this assay. The cells with basal level of cellular cholesterol may be cholesterol enriched by culturing with cholesterol donors.

"A cholesterol donor" is a lipoprotein that delivers cholesterol into cells via the receptor-mediated LDL pathway. Suitable cholesterol donors include, but are not limited to, acetyl LDL (acLDL), oxidized (oxLDL), native LDL, aggregated LDL, and derivatives thereof.

"An ACAT inhibitor" is a compound that inhibits the acyl CoA:cholesterolacyl transferase (ACAT) from esterifying free cholesterol. Compounds that retain ACAT inhibiting activity include, but are not limited to, CP-113,818 (Pfizer Pharmaceuticals) and 58-035 (Sandoz Pharmaceuticals).

The term "therapeutic agent" refers to any agent given to a subject to treat, ameliorate or prevent atherosclerosis or other cholesterol or lipid-related disorders. Exemplary agents include, but are not limited to, cholesterol lowering drugs such as Lipitor®

Cholesterol Clearance Potential

The movement of cholesterol from cells to serum or interstitial fluid, known as reverse cholesterol transport, is mediated primarily through the action of HDL, a cholesterol acceptor, coupled with serum enzymes such as cholesterol ester transfer protein and lecithin cholesterol acyl-transferase (LCAT). It has been proposed that this reverse cholesterol transport function of HDL imparts its protective effects against the development of atherosclerosis. Great efforts have been made to develop pharmaceutical agents that modify the lipoprotein profile in the serum, therefore stimulating the cholesterol clearance.

According to the present invention, a standard assay is developed to determine the cell cholesterol clearance potential of a serum sample. More specifically, the assay is carried out by exposing cholesterol enriched cells to a serum sample obtained from a subject and quantifying net cholesterol flux in the cholesterol enriched cells after the exposure to the serum sample, wherein a reduction of the cellular cholesterol mass compared to that determined prior to the exposure correlates with the cholesterol clearance potential of the serum sample. Alternatively, the HDL-containing fraction of the serum sample, wherein apoB containing lipoprotein are removed, are used in the present invention.

Also provided herein are kits that are used to carry out the assay presented herein. These kits generally contain cholesterol enriched cells, cell culture media, cell culture tubes or multi-well plates, and reagents used in the measurement of cellular cholesterol mass. In certain embodiment of the present invention, a kit may comprises cells that retain one or more LDL-receptors on their cell surfaces, a cholesterol donor, cell culture media, cell culture tubes or multi-well plates, and reagents used in the measurement of cellular cholesterol mass. Alternatively, the kit may further comprises an ACAT inhibitor.

The following examples are provided to illustrate an embodiment of the invention. It is not intended to limit the invention in any way.

EXAMPLE I

Cholesterol Clearance Assay

The reproducibility of this cholesterol clearance assay using human serum and HDL isolated from human plasma was investigated. In these series of experiments, THP-1 macrophage cells are enriched with cholesterol (basal level=20 μg cholesterol/mg cell protein, enriched=80–100 μg cholesterol/mg cell protein) by incubation with acLDL (100 mg/ml) for 48 hours. The data represented in FIG. 1 are from experiments performed using a single pool of human serum collected from healthy individuals or a single batch of HDL isolated from fresh human plasma.

EXAMPLE II

Correlation to HDL Parameters

Figure 2:
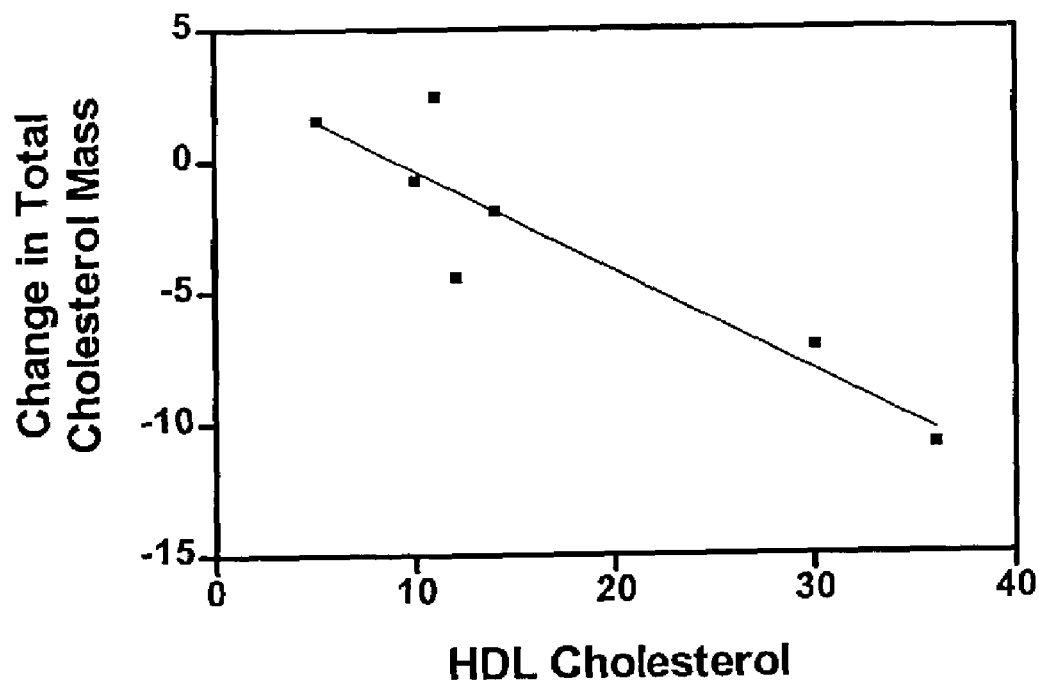
FIG. 2 is a graph showing that a correlation exists between reduction in cellular cholesterol mass and increasing HDL cholesterol concentration levels. THP-1 macrophage cells were cholesterol enriched with 100 μg/ml acLDL for 48 hours. The cells were then incubated with 10% human serum from 7 individuals for 48 hours. Cholesterol mass was measured by GLC and values were normalized to total cell protein. Values are expressed as percent change relative to acLDL alone (no acceptor) set at zero.
Figure 3:
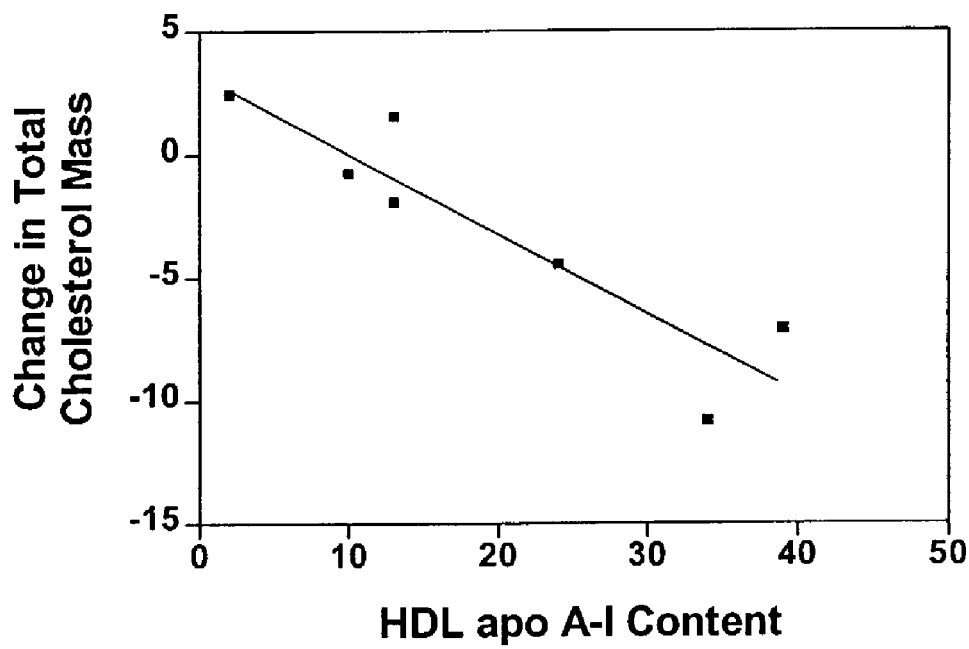
FIG. 3 is a graph showing that a correlation exists between reduction in cellular cholesterol mass and increasing HDL apolipoprotein A-I concentration levels. THP-1 macrophage cells were cholesterol enriched with 100 μg/ml acLDL for 48 hours. The cells were then incubated with 10% human serum from 7 individuals for 48 hours. Cholesterol mass was measured by GLC and values were normalized to total cell protein. Values are expressed as percent change relative to acLDL alone (no acceptor) set at zero.

The assay of the present invention provides an accurate assessment of differences in human serum samples with varying HDL concentrations. The human serum samples shown in FIGS. 2 and 3 were diluted into tissue culture media at a concentration of 10%. FIGS. 2 and 3 demonstrate the correlation between cellular cholesterol mass reduction and serum HDL cholesterol concentration (FIG. 2), and HDL apolipoprotein A-I concentration (FIG. 3). Thus, this assay is useful in determining the contribution of different acceptors on cholesterol clearance between clinical samples.

EXAMPLE III

Cholesterol Clearance Assay in Unesterified Cholesterol-Enriched Cells

Figure 4:
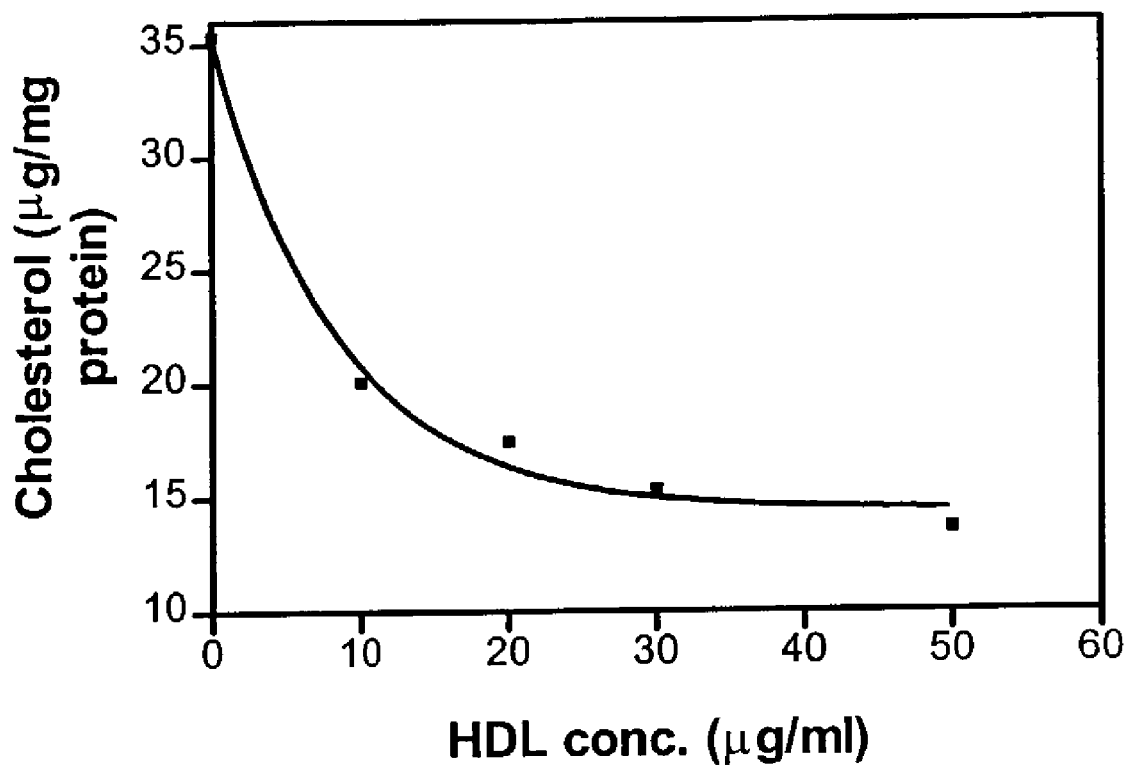
FIG. 4 is a graph showing unesterified cholesterol clearance. THP-1 macrophage cells were cholesterol enriched with unesterified cholesterol/phospholipid dispersions (250 μg cholesterol/ml) for 24 hours. The cells were then incubated with human $HDL_3$ at the indicated concentrations for 24 hours. Cholesterol mass was measured by GLC and values were normalized to cell protein. Values are expressed as mass of unesterified cholesterol per mg of cell protein. ACAT inhibitor CP-113,818, Pfizer Pharmaceuticals, Groton Conn.

In a further embodiment of the invention, a net cholesterol flux assay that can be utilized to measure unesterified cholesterol mass reduction from THP-1 macrophage cells was developed. This assay is efficient, cost effective, and can be used when a researcher does not necessarily desire to have esterified cholesterol in the cells. In this system, THP-1 macrophage cells are incubated with free cholesterol/phospholipid dispersions in the presence of an acyl CoA:cholesterol acyl transferase (ACAT) inhibitor. This allows for the accumulation of unesterified cholesterol without allowing ACAT, the enzyme that is responsible for the esterification of cholesterol to function. The unesterified cholesterol content of the cells increases from 20 μg cholester/mg cell protein to 60–70 μg cholesterol/mg cell protein with no detectable esterified cholesterol. Additionally, the cholesterol enrichment period is 24 hours, compared to the 48 hours used in the assay with esterified cholesterol. After an equilibration period, the cells are exposed to an acceptor for 8–24 hours. Like the assay described in the previous example, FIG. 4 shows that this assay is sensitive over a range of HDL concentrations.

EXAMPLE IV

Figure 5:
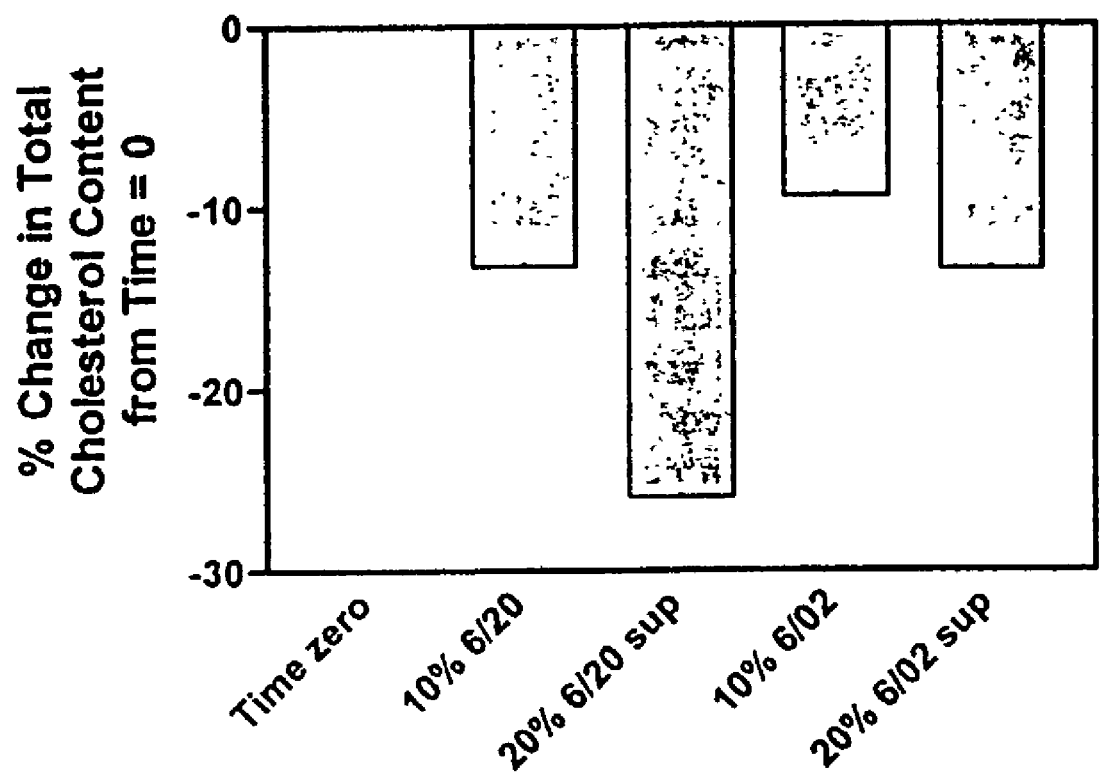
FIG. 5 is a graph showing the results on cholesterol flux following incubation of various acceptors with THP-1 macrophage foam cells. THP-1 macrophage were cholesterol enriched with 100 μg/ml acLDL for 48 hours. The cells were then incubated with 10% of the supernatant generated after precipitating the apoB containing lipoprotein with PEG for 48 hours. Cholesterol mass was measured by GLC and values were normalized to cell protein. Values are expressed as percent change relative to acLDL alone (no acceptor) set at zero.

The Use of Cholesterol Clearance Assay with ApoB Lipoprotein Deprived Clinical Samples In this example, cholesterol enriched THP-1 macrophage cells are incubated for 48 hours with HDL-containing supernatant following removal of apoB lipoprotein. FIG. 5 shows the results from such an experiment. As shown, both pools of human serum tested caused a significant decrease (9–13%) in the mass of cholesterol in the THP-1 foam cells. Furthermore, both HDL-containing supernatant were more effective (13–27%) in promoting cholesterol clearance than their corresponding whole serum samples.

EXAMPLE V

Improved Protocol for Removing ApoB Lipoproteins from Serum

Figure 6:
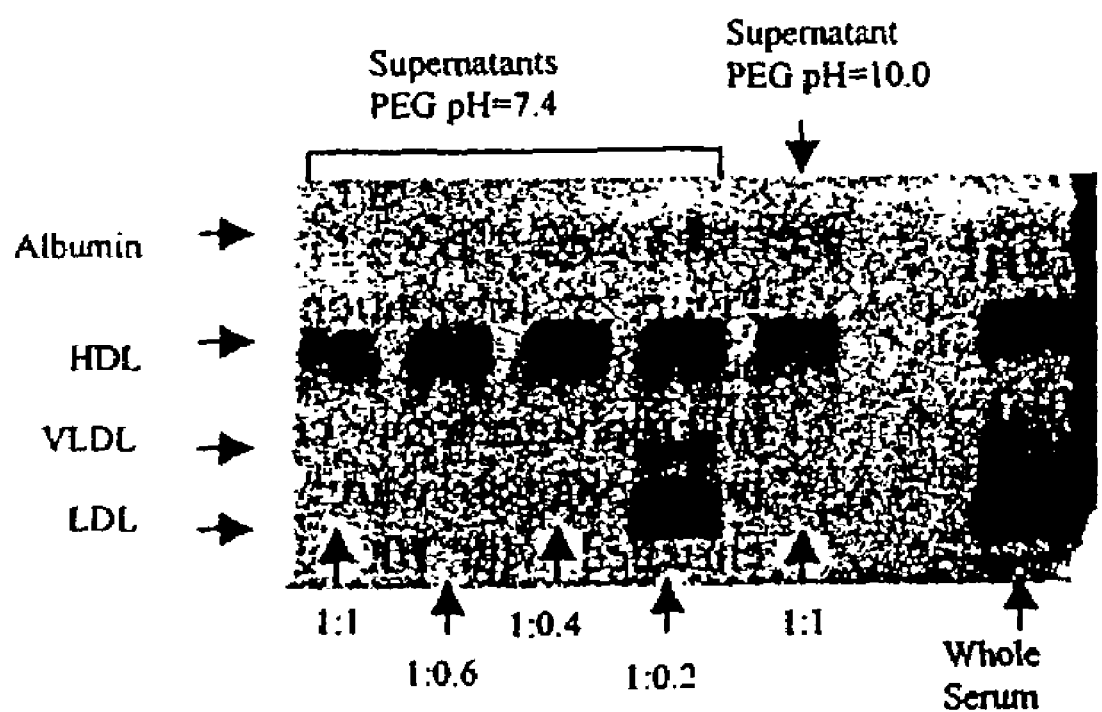
FIG. 6 is a gel demonstrating removal of LDL and VLDL with PEG. A 20% PEG (pH=10.0 or 7.4) solution was added to serum at a 1:1, 1:0.6, 1:0.4, or 1:0.2 (serum to reagent) ratio and incubated at room temperature for 15 minutes. The solution was then centrifuged at 4000 rpm (1900g) for 20 minutes at 4° C. The supernatant were run on a LipoGel system (Beckman Coulter, Fullerton, Calif.).

The supernatant generated from precipitation of apoB containing lipoprotein is not toxic to cells and does not interfere with the uptake of acLDL into THP-1 macrophage cells. One complication associated with this procedure is exposing serum to the the high pH required to solubilize PEG (pH=10). The published procedure was modified and the pH of the PEG reagent was adjusted to 7.4 prior to serum addition. FIG. 6 illustrates that this process effectively removed LDL and VLDL from the serum. Additionally, the amount of reagent added to the serum sample can be reduced to a 1:0.4 (serum to reagent) ratio and still effectively remove the LDL and VLDL.

REFERENCES

1. Johnson, W. J., F. H. Mahlberg, G. H. Rothblat, and M. C. Phillips. 1991. Cholesterol transport between cells and high density lipoproteins. *Biochim. Biophys. Acta* 1085: 273–298.
2. Johnson, W. J., M. J. Bamberger, M. J. Latta, R. A. Rapp, M. C. Phillips, and G. H. Rothblat. 1986. The bidirectional flux of cholesterol between cells and lipoproteins. *J. Biol. Chem.* 261:5766–5776.
3. Small, D. M. 1988. Progression and regression of atherosclerotic lesions. *Artero.* 8:103–129.
4. Shio, H., N. J. Haley, and S. Fowler. 1978. Characterization of Lipid-laden aortic cells from cholesterol-fed rabbits II. Morphometric analysis of lipid-filled lysosomes and lipid droplets in aortic cell population. *Laboratory Investigation* 39:390–397.
5. Hakamata, H., A. Miyazaki, M. Sakai, Y. Suginohara, Y.-I. Sakamoto, and S. Horiuchi. 1994. Species difference in cholesteryl ester cycle and HDL-induced cholesterol efflux from macrophage foam cells. *Arterioscler. Thromb.* 14:1860–1865.
6. Bernard, D. W., A. Rodriguez, G. H. Rothblat, and J. M. Glick. 1991. cAMP stimulates cholesteryl ester clearance to high density lipoproteins in J774 macrophages. *J. Biol. Chem.* 266:710–716.
7. Contreras, J. A. and M. A. Lasunción. 1994. Essential differences in cholesteryl ester metabolism between human monocyte-derived and J774 macrophages: Evidence against the presence of hormone-sensitive lipase in human macrophages. *Arterioscler. Thromb.* 14:443–452.
8. Hakamata, H., A. Miyazaki, M. Sakai, Y.-I. Sakamoto, H. Matsuda, K. Kihara, and S. Horiuchi. 1995. Differential effects of an acyl-coenzyme A:cholesterol acyltransferase inhibitor on HDL-induced cholesterol efflux from rat macrophage foam cells. *FEBS* 363:29–32.
9. Miyazaki, A., M. Sakai, Y. Suginohara, H. Hakamata, Y.-I. Sakamoto, W. Morikawa, and S. Horiuchi. 1994. Acetylated low density lipoprotein reduces its ligand activity for the scavenger receptor after interaction with reconstituted high density lipoprotein. *J. Biol. Chem.* 269:5264–5269.

What is claimed is:

1. A method for determining the effect of a therapeutic agent on altering net cholesterol mass flux comprising the steps of:
   a) obtaining a first serum sample from a subject;
   b) determining the net cholesterol mass flux mediated by a first serum sample by
      a') providing cholesterol containing cells;
      b') quantifying a first cellular cholesterol mass for said cholesterol containing cells;
      c') exposing said cholesterol containing cells to a serum sample for a period of time sufficient enough to allow cholesterol flux to occur;
      d') quantifying a second cellular cholesterol mass for said cholesterol containing cells after the exposure to said serum sample; and
      e') comparing said first and second cellular cholesterol mass, wherein an alteration of said second cellular cholesterol mass compared to said first cellular cholesterol mass indicates the capacity of the said serum sample to cause net cholesterol mass flux;
   c) administering an effective amount of said therapeutic agent to said subject;
   d) obtaining a second serum sample from said subject after the administration of said therapeutic agent;
   e) determining the net cholesterol mass flux mediated by the second serum sample by the assay according to steps a') through e'); and
   f) comparing said first and second net cholesterol mass flux, wherein an alteration of said second net cholesterol mass flux compared to the first net cholesterol mass flux indicates the capacity of said therapeutic agent to influence net cholesterol mass flux.

2. The method as claimed in claim 1, wherein said therapeutic agent increase net cholesterol mass flux.

3. The method as claimed in claim 1, wherein said therapeutic agent decreases net cholesterol mass flux.

* * * * *